US00PP33504P2

(12) United States Plant Patent
Whitcomb

(10) Patent No.: US PP33,504 P2
(45) Date of Patent: Sep. 21, 2021

(54) INDIAN GRASS PLANT NAMED 'WHIT LXXI'

(50) Latin Name: *Sorghastrum nutans*
Varietal Denomination: Whit LXXI

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 17/131,885

(22) Filed: Dec. 23, 2020

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
(74) *Attorney, Agent, or Firm* — Jeffrey Streets

(57) ABSTRACT

A new and distinct variety of Indian grass, *Sorghastrum nutans*, designated cultivar 'Whit LXXI' substantially as illustrated and described herein having distinct blue-grey foliage and compact stature with stout culms supporting rusty-tan colored flower plumes beginning in mid-summer. This new cultivar is characterized by a transitioning growth habit during the growing season, beginning with blue-grey foliage, dwarf stems that grow about 16 to 25 inches tall during spring to mid-summer, then dense tufts of flowering culms supporting additional blue-grey leaves making the plant foliage about 30 to 40 inches tall, continuing with the extension of plume like very upright rusty-tan seed heads 46 to 58 inches tall. The new variety of Indian grass is a distinctly superior seedling selected from multiple generations of seedlings resulting from research that began in 1997.

3 Drawing Sheets

Genus, species: *Sorghastrum nutans*.
Varietal denomination: 'Whit LXXI'.

BACKGROUND OF THE INVENTION

Field of the Invention

The present invention relates to a new and distinct variety or cultivar of the native perennial prairie grass, *Sorghastrum nutans*, commonly known as Indian grass.

Description of the Related Art

*Sorghastrum nutans* is native to a broad range of North America from southern Canada to Mexico. *Sorghastrum nutans* is especially prominent in what is commonly referred to as the prairie corridor.

Indian grass is a clump-forming hardy perennial with an annual top. Indian grass is one of the four major grasses populating the great plains along with big bluestem, *Andropogon gerardii*; little bluestem, *Schizachyrium scoparium*; and switchgrass, *Panicum virgatum*.

The new variety of Indian grass claimed herein, which has been given the cultivar name 'Whit LXXI', is a seedling selected from a block of about 30 open pollinated seedlings from a single parent planted near Stillwater, Okla. in July 2016. The parent was 11 generational descendants from the original plant from which seed was saved to begin this research in 1997. With each successive generation, seeds were saved from a few of the most promising plants, leading to the specific parent of 'Whit LXXI'. Seed viability has remained very low in this genetic line, with seedling numbers ranging from 9 to 46. An advantage is that seeds from 'Whit LXXI' are unlikely to become invasive. The new cultivar of Indian grass, 'Whit LXXI', has foliage distinctly more bluish grey versus the parent or any of the other seedlings from that parent or seedlings from previous parents.

This new and distinct Indian grass was asexually reproduced by divisions removed from the original 'Whit LXXI' clump growing near Stillwater, Okla. The asexually reproduced plants showed all of the unique features that characterize this Indian grass. As a secondary test, divisions were made from the first set of plants grown from divisions. These secondary division plants also grew the same as the parent, confirming the unique features of this new plant are stable through successive generations of asexual propagation.

SUMMARY OF THE INVENTION

The plant of the present invention is a new and distinct variety of Indian grass, *Sorghastrum nutans*, which has been given the cultivar name 'Whit LXXI'. It is characterized by a transitioning growth habit during the growing season, beginning with blue-grey foliage, semi-dwarf stems that grow about 16 to 25 inches tall during spring to mid-summer, then in late-summer, grow dense tufts of flowering culms supporting additional blue-grey leaves, making the plant foliage 30 to 40 inches tall, continuing with extension of plume-like very upright seed heads, 46 to 58 inches tall.

BRIEF DESCRIPTIONS OF THE DRAWINGS

DETAILED BOTANICAL DESCRIPTION

The following is a botanical description of the new and distinct Indian grass plant, *Sorghastrum nutans*, which has been given the cultivar name 'Whit LXXI'. Specific color designations set forth by number designations are in accordance with The Royal Horticultural Society Colour Chart (1966). General color recitations are consistent with ordinary American color terminology.

The plant:

*Type*.—Deciduous clump forming perennial grass plant.

*Classification*.—Indian grass, *Sorghastrum nutans*.

Figure 1:
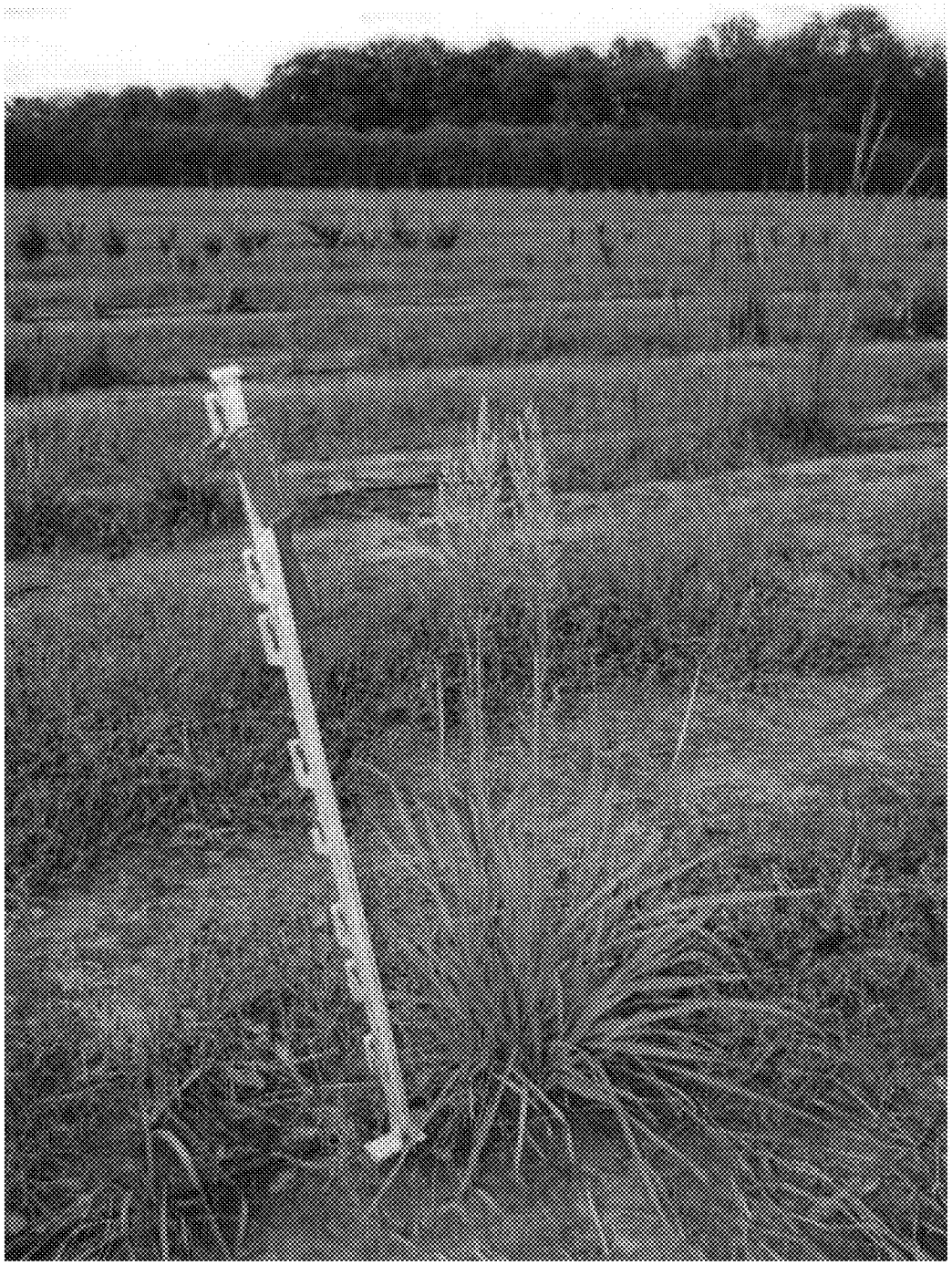
FIG. 1 is a full color view of the new and distinct Indian grass plant given the cultivar name 'Whit LXXI' showing the blue-green foliage, growth habit and flowering of a one-year-old plant propagated from the original parent.
Figure 2:
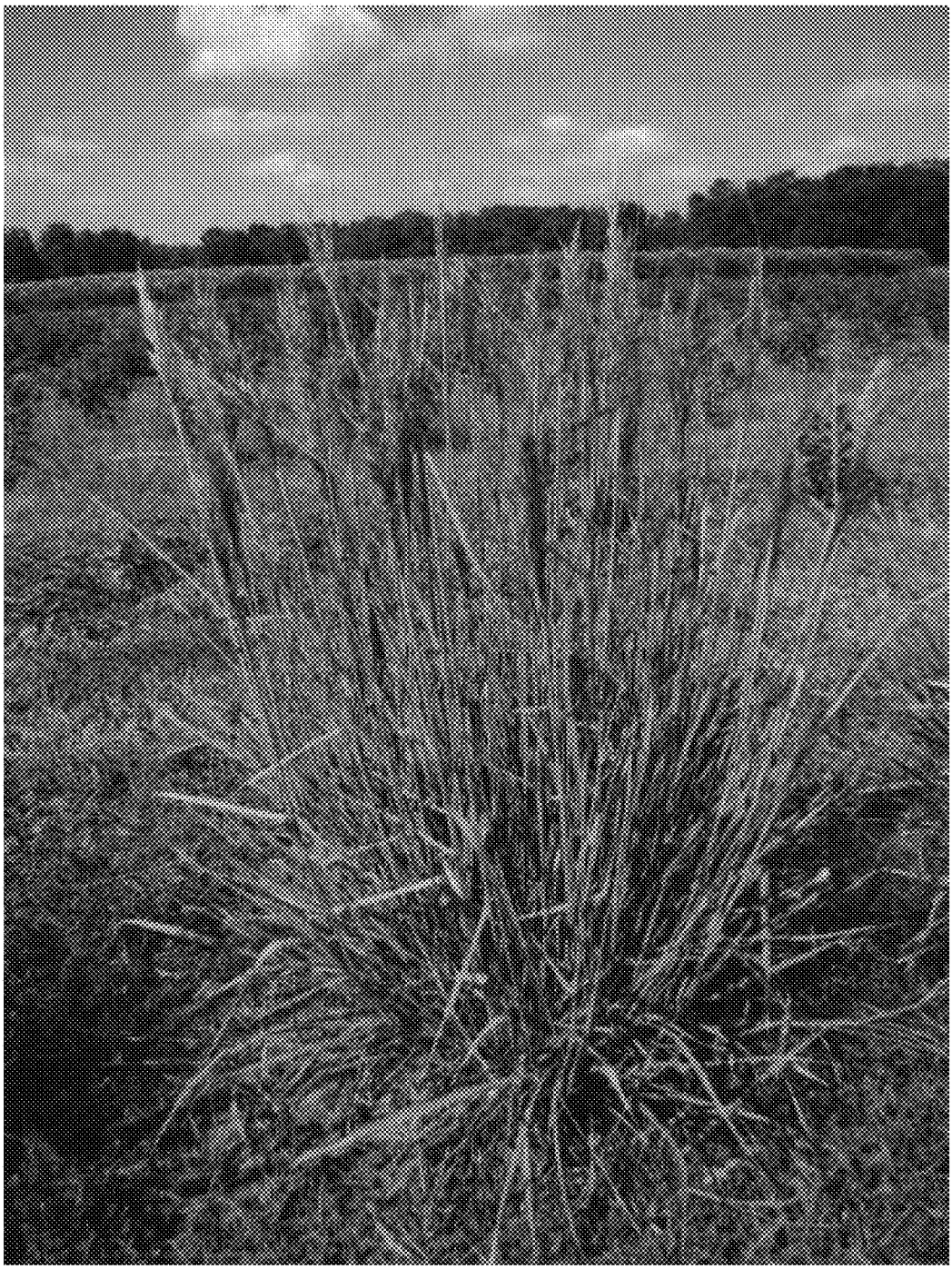
FIG. 2 is a full color view of the new and distinct Indian grass plant given the cultivar name 'Whit LXXI' showing a three-year-old plant with large concentration of leaves from the culms creating a dense mass of blue-green foliage beneath the recently emerged panicles of flowers.
Figure 3:
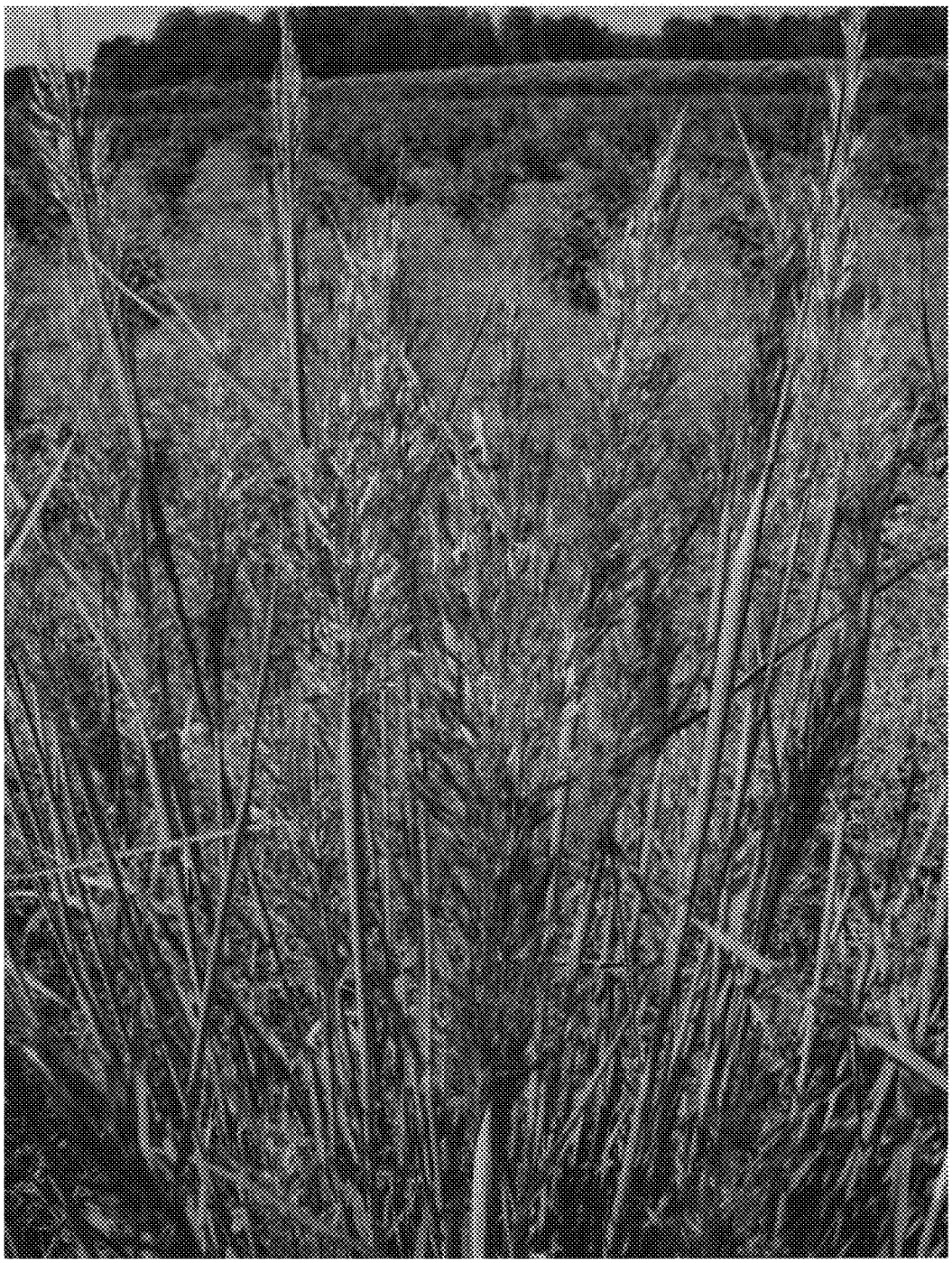
FIG. 3 is a full color view of the new and distinct Indian grass plant given the cultivar name 'Whit LXXI' showing the plume-like rusty-tan seed heads.

*Growth habit*.—Clump-forming perennial grass plant developing dense multiple stems with flowering panicles rising above distinct blue-grey foliage. One year old plants typically produce 1 or 2 flower culms, (FIG. 1), whereas three-year-old plants produce from 50 to 80, (FIG. 2). Specific clump size cannot be stated as the clump increases a few inches in diameter each growing season. Plant size is approximately 6 to 8 inches in diameter at the end of one growing season, and about 16 to 18 inches in diameter at the base after three growing seasons under conditions of good soil and moderate fertilizer. Growth would be expected to be less under poor soil conditions or more with a higher rate of fertilizer.

*Origin*.—The new variety of Indian grass is a distinctly superior seedling selected from a block of about 30 open pollinated seedlings from a single parent planted near Stillwater, Okla. in July 2016. The parent was an 11 generational descendant from the original parent from which seed was used to begin this research in 1997. The original parent was a wild plant, native on the farm and not a cultivar and not having been grown in cultivation before I began this research. With each successive generation, seeds were saved from a few most promising plants, leading to the specific parent of 'Whit LXXI'. Seed viability has remained very low in this genetic line, with seedling numbers ranging from 9 to 46. Seeds collected from 'Whit LXXI' in 2017, 2018, 2019 and 2020 either had no germination or produced only a few weak seedlings that did not survive transplanting. An advantage is that seeds from 'Whit LXXI' are unlikely to become invasive.

*Propagation*.—Propagation is by dividing the clump using pieces of each rhizome to create a new plant. Successive propagation of this plant has shown that the plant is stable through multiple reproductions.

*Hardiness*.—The new variety of Indian grass was developed beginning with seed from a single plant in a native population near Stillwater, Okla. in 1997. Indian grass, *Sorghastrum nutans* is native from southern Canada to northern Mexico. It is estimated that this specific plant will be cold hardy from zone 3 through 9.

*Pests and disease*.—Having known and observed native populations of Indian grass for over 60 years and working closely with the genetic line in this research for over 20 years, no disease or insect problems have been observed.

The flowers:

*Blooming period*.—Flower emergence from the culms typically begins in mid-summer in North Central Oklahoma. Flower panicles remain showy through fall, about 3 to 3.5 months in north central Oklahoma, and remain showy after a freeze and into early winter.

*Flowers*.—Mature seed heads are plume-like, covered with dense spikelets, rusty-tan, about 165 B or C or 164 A or B, on sturdy culms extending just above the foliage (FIG. 2) with each culm having 2 to 6 leaves. Individual panicles of flowers are variable and range from 7 to 14 inches tall and about 0.75 to 1.6 inches diameter in the cylindrical center section comprising about ⅔ of the overall length, then tapering to the apex and base. Newly emerged flower spikes are briefly greenish, about 151 A or B, soon changing to about 182 A or B, then quickly transitioning to about 165 A, B or C or 174 A or B with maturity. Spikelets and individual florets are variable with deformed glumes, lemma and palea surrounding what appear as remnant deformed seed. A few yellow anthers, about 15 A or B, are visible for 24 to 30 hours before dropping. After selecting this cultivar named 'Whit LXXI', plumes were collected in 2017 and 2018, cleaned, and the few seeds separated from the chaff. None germinated. However, using the same collection process in 2019 a few weak and stunted seedlings were produced, but none survived transplanting. Seeds were also collected in Fall of 2020 and planted Spring 2021, with only two weak seedlings. Failure to produce viable seedlings is an advantage to an ornamental grass making it unlikely to be invasive. Attempts to identify the various flower parts is not possible due to the various deformities. The plant is nearly sterile, under conditions that exist out of doors in north central Oklahoma producing only a few week seedlings that have not survived transplanting. The plant has not been isolated as other Indian grass plants growing in the same or adjacent rows should provide ample pollination opportunities.

The foliage and form: When growth emerges in spring, new leaves from the crown are mostly upright, transitioning to more arching with winds and rains creating a rounded mound 16 to 25 inches tall until mid-summer when flowering culms begin to appear. Culms are hollow yet sturdy and erect. Leaves developing on the culms range from 2 to 6, are alternate, about 4 to 10 inches apart, length variable, about 4 to 24 inches long, 0.4 to 0.6 inches wide, mostly flat, rough textured on both surfaces, arching outward and tapering to a sharp point at the tip. As the flowering culms appear and junction with the leaf sheaths, the overall size of the foliage mass is about 30 to 40 inches tall, then with the extension of the flowering panicles reach a height of about 46 to 58 inches tall (see FIG. 2). Leaf color is a distinct bluish-green, most pronounced with early emergence, about 122 A, B or C, ranging to 189 B or C on both upper and lower leaf surfaces with little change across the leaf surface above or below and remaining during the growing season until a frost when color changes abruptly to 165 A or B or 177 B or C. Leaves are long, lanceolate with parallel veins with little or no variation in leaf color across the leaf or along the length of the leaf and on both upper and lower leaf surfaces including the mid-vein. Leaf margin is finely serrate with leaves produced early in the growing season becoming less so as the season progresses.

I claim:

1. A new and distinct variety of Indian grass, *Sorghastrum nutans*, named 'Whit LXXI', substantially as illustrated and described herein.

* * * * *